United States Patent
Patel et al.

(10) Patent No.: US 7,115,969 B1
(45) Date of Patent: Oct. 3, 2006

(54) FIXED PARALLEL PLATE MEMS CAPACITOR MICROSENSOR AND MICROSENSOR ARRAY AND METHOD OF MAKING SAME

(75) Inventors: Sanjay V. Patel, San Diego, CA (US); Bernd Fruhberger, Encinitas, CA (US); Erno Klaassen, Sunnyvale, CA (US); Todd E. Misna, Carlsbad, CA (US); David R. Baselt, San Diego, CA (US)

(73) Assignee: Xsilogy, Inc., San Diego, CA (US)

( * ) Notice: Subject to any disclaimer, the term of this patent is extended or adjusted under 35 U.S.C. 154(b) by 260 days.

(21) Appl. No.: 10/242,966

(22) Filed: Sep. 13, 2002

(51) Int. Cl.
*H01L 29/00* (2006.01)
(52) U.S. Cl. .................................................. 257/532
(58) Field of Classification Search ................ 257/532, 257/295–310
See application file for complete search history.

(56) References Cited

U.S. PATENT DOCUMENTS

| | | | |
|---|---|---|---|
| 6,724,612 B1 * | 4/2004 | Davis et al. | 361/328 |
| 6,812,821 B1 * | 11/2004 | Fujita et al. | 338/34 |
| 2002/0105080 A1 * | 8/2002 | Speakman | 257/749 |

* cited by examiner

*Primary Examiner*—Cuong Nguyen
(74) *Attorney, Agent, or Firm*—BioTechnology Law Group; Daniel M. Chambers (57) ABSTRACT

A fixed parallel plate micro-mechanical systems (MEMS) based sensor is fabricated to allow a dissolved dielectric to flow through a porous top plate, coming to rest on a bottom plate. A post-deposition bake ensures further purity and uniformity of the dielectric layer. In one embodiment, the dielectric is a polymer. In one embodiment, a support layer is deposited onto the top plate for strengthening the sensor. In another embodiment, the bottom plate is dual-layered for a narrowed gap. Integrated circuit arrays of such sensors can be made, having multiple devices separated from each other by a physical barrier, such as a polycrystalline containment rim or trough, for preventing polymer material from one sensor from interfering with that of another.

8 Claims, 12 Drawing Sheets

FIXED PARALLEL PLATE MEMS CAPACITOR MICROSENSOR AND MICROSENSOR ARRAY AND METHOD OF MAKING SAME

BACKGROUND OF THE INVENTION

1. Field of the Invention

The present invention is directed to chemical microsensors. More particularly, the present invention is directed to fixed parallel plate chemical microsensors and microsensor arrays and methods of making same.

2. Background Information

Sensors based on micro electromechanical systems (MEMS) devices are useful for sensing a wide range of chemical conditions, such as the presence of volatile organic compounds (VOCs), hydrocarbon gases, and other analytes. Manufacturing techniques for building MEMS sensors, especially integrated circuit arrays of such sensors, usually involve many fabrication steps. Unfortunately most, if not all, of the sensor functionality has to be built into the microchip up front, making it difficult to customize or tune a sensor to fit a particular need after manufacture. For example, the dielectric material of a parallel plate capacitor sensor is usually deposited onto a first conductive electrode during an intermediate phase of the fabrication process, followed by deposition of a top plate electrode. Furthermore, MEMS devices are typically manufactured with solid dielectric materials whose physical properties require that layers be deposited in a specified order.

Other MEMS device configurations can be used as well to sense chemicals, for example, by measuring the capacitance changes of chemically sensitive materials with an interdigitated finger capacitor or changes in physical properties with a cantilever. However, these arrangements often call for semi-rigid or flexible conductors that suffer from several disadvantages, including excess stray capacitance, stiction, and sensitivity to vibrations.

SUMMARY OF THE INVENTION

The devices and methods of the present invention overcome the aforementioned disadvantages by providing a fixed parallel plate capacitor microsensor that comprises a porous top plate, a bottom plate, and a chemically absorbent dielectric material in between. In one embodiment, the dielectric material is a dissolved polymer deposited onto the porous top plate and permitted to flow through the pores, creating a uniform coat on the bottom plate and substantially filling an etched sensing gap created between the plates by a previous process.

In another embodiment, the dissolved polymer dielectric is deposited onto the device by spin coating, spray coating, or dip coating. In yet another embodiment, the dissolved polymer dielectric is baked in an oven after deposition. In still another embodiment, one or more support layers is deposited on the device for added structural support.

In one embodiment, a plurality of fixed parallel plate capacitor microsensors is micromachined onto a substrate to create an array of devices for varying the sensitivity and/or selectivity of the array. Included in this embodiment is a network of containment barriers, such as a rim or a trough, for containing dielectric material between devices.

DETAILED DESCRIPTION OF THE PREFERRED EMBODIMENTS

The devices and methods of the present invention overcome the drawbacks inherent with current MEMS devices and fabrication techniques by providing a fixed parallel plate capacitor that reduces or eliminates such operational side effects as dielectric swelling. In addition, fabrication of a parallel plate capacitor sensor is made more flexible by allowing dielectric deposition to occur after the device is manufactured. This allows preparation of sensors with many different dielectric properties and materials characteristics. The dielectric material flows through the openings of a porous top plate, coming to rest on the device bottom plate, as further described to follow.

Figure 1:
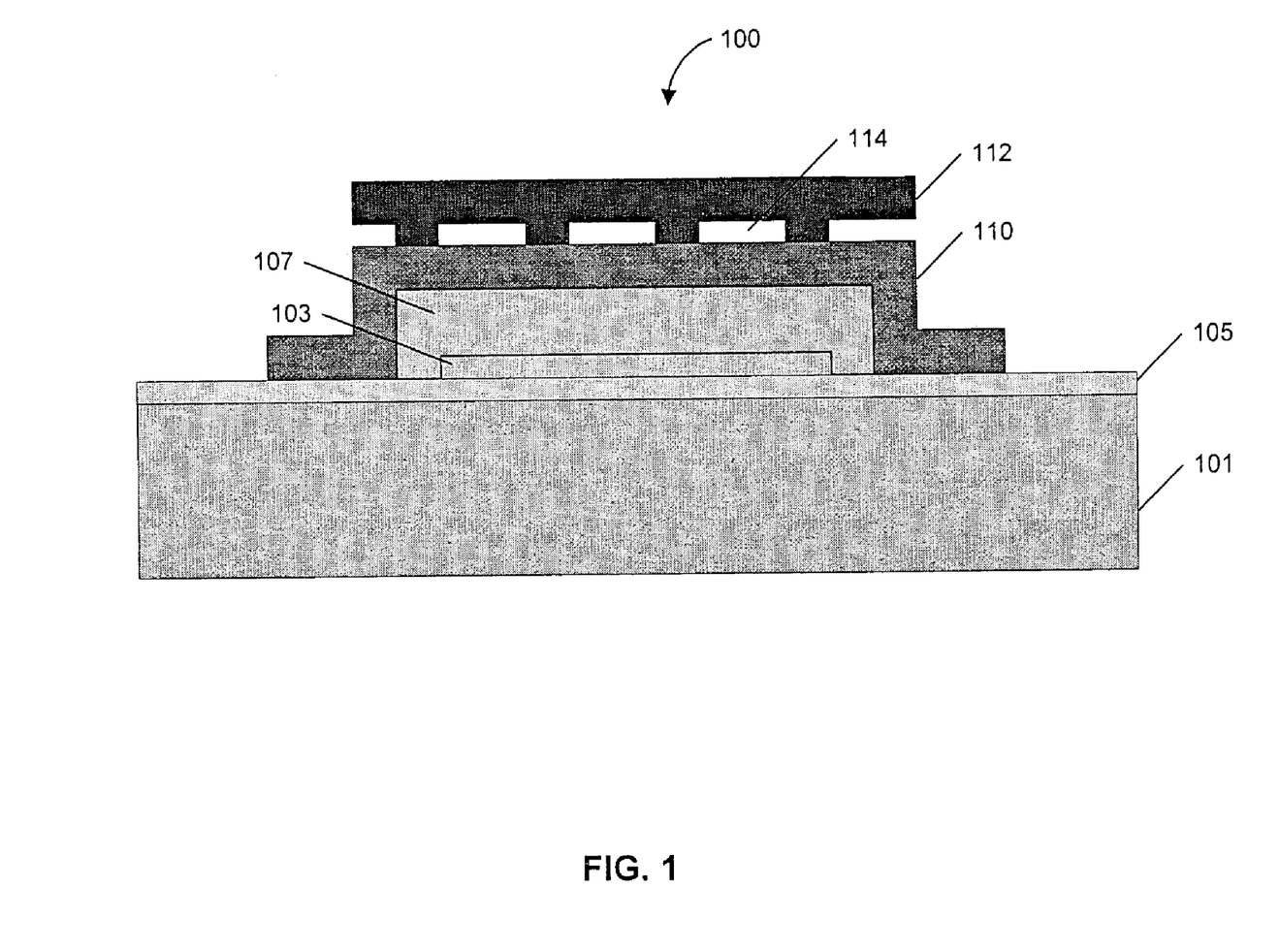
FIG. 1 is a cross-sectional view of a fixed parallel plate capacitor sensor having a support layer and designed in accordance with the devices and methods of the invention.

FIG. 1 is a cross-sectional view of a fixed parallel plate capacitor sensor 100 having a porous top plate electrode and designed in accordance with the devices and methods of the present invention. Capacitor sensor 100 can be easily manufactured using standard photolithographic techniques, such as by creating vias where individual layers require contact or by using hydrofluoric acid to etch away sacrificial layers. Capacitor sensor 100 is a layered device comprising bottom plate 103, porous top plate 110, dielectric 107, and built on substrate 101 to be electrically isolated therefrom by isolation layer 105. Support layer 112 is deposited onto porous top layer 110 to provide strength to capacitor sensor 100.

Dielectric 107 is made from a chemically absorbent material that changes permitivity in the presence of a chemical, such as a target analyte. In one embodiment, dielectric 107 is a non-conductive material such as a polymer, solgel, or ceramic. In other embodiments, dielectric 107 is made of a semi-conductive material, such as a composite of a polymer and an ionic or electronic conductor.

In one embodiment, bottom plate 103 is a conductive material, such as polycrystalline silicon. In another embodiment, bottom plate 103 is a conductive material, such as a metal. Similarly, porous top plate 110 is in one embodiment a conductive material, such as polycrystalline silicon, while in other embodiments, top plate 110 is made of a conductive material such as a metal.

Top plate 110 is porous in order to permit the cavity between top plate 110 and bottom plate 103 to be coated with a viscous dielectric fluid during a deposition process according to the methods described herein. Top plate 110 can be made of a conductor that is innately porous, or top plate 110 can be made porous during fabrication, by patterning injection holes across the plate surface.

Support layer 112 can be a conductive material such as polycrystalline silicon, or other flexible or semi-rigid material that prevents device sub-layers from collapsing or bending. In one embodiment, support layer 112 is made from polycrystalline silicon. Support layer 112 can be patterned with gaps 114 separating the support layer from top plate 110, as shown or support layer 112 can be a solid layer, contacting top plate 110 of capacitor sensor 100 over the entire surface of top plate 110, for added strength. Support layer 112 can be deposited onto top plate 110 by etching away vias at those locations on top plate 110 where contact between top plate 110 and support layer 112 is desired.

Figure 2:
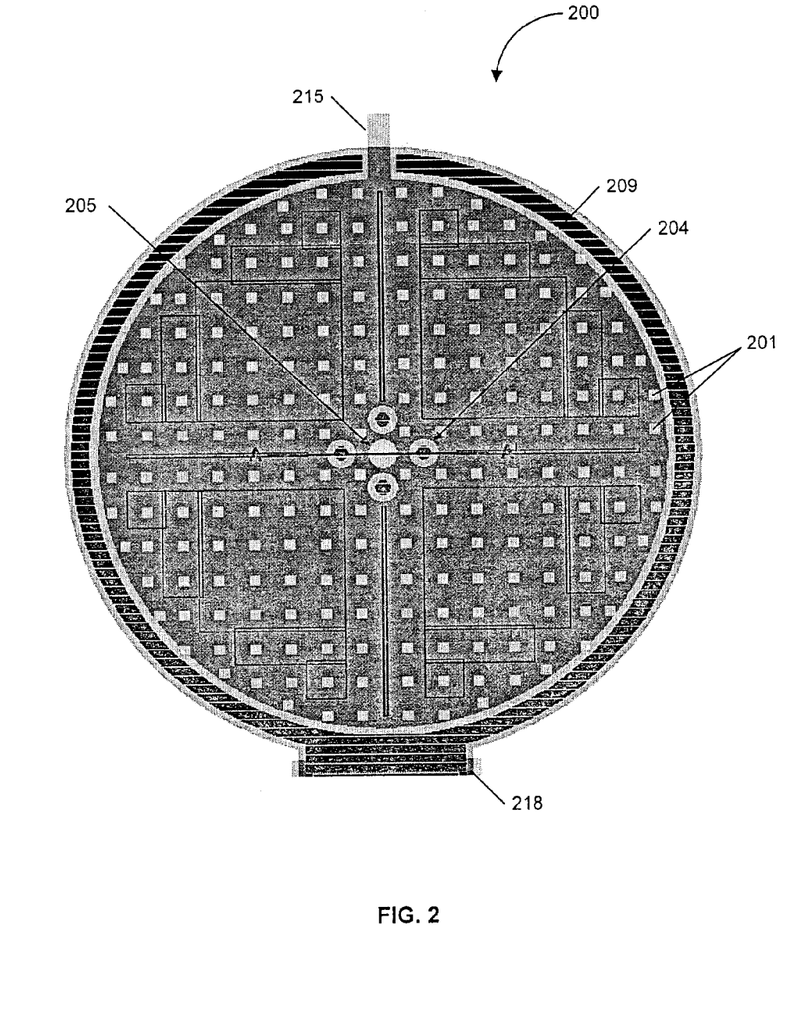
FIG. 2 is a top-level view of a circular-shaped fixed parallel plate capacitor sensor having no support layer and implemented according to an embodiment of the invention.

FIG. 2 is a top-level view of a circular-shaped fixed parallel plate capacitor sensor 200 implemented according to an embodiment of the present invention. In this implementation, capacitor sensor 200 comprises a network of pores 201 interspersed across the surface of top-plate 110, thus creating the porosity needed to allow dielectric injection onto bottom plate 103, escape paths for the displaced air, and to further permit absorption of atmosphere later during device operation. In one embodiment, central fill hole 205, generally larger in size than pores 201, is used to permit drops of dielectric to flow easily underneath top plate 110 during dielectric deposition.

An array of anchors 204 affixes top plate 110 to substrate 101 and prevents collapse of top plate 110 onto bottom plate 103. Anchors 204 are provided for support and can be placed across the surface of the capacitor in many different configurations, including the configuration shown in FIG. 2 having four anchors near to and surrounding fill hole 205. In a typical case, the outer perimeter 209 of capacitor 200 also comprises a continuous anchor around the device perimeter to provide support at the edges. Anchors 204 provide device stiffness to help counteract polymer swelling during sensor operation, and are chiefly responsible for making porous top plate 110 fixed with respect to bottom plate 103. Anchors 204 can be vias made by etching away the same sacrificial layer that produces the sensing gap between top plate 110 and bottom plate 103.

Bottom plate 103 in this implementation is a drive electrode that spans the bottom surface of the device, the continuity of which is interrupted only at those points where top plate 110 is pierced by an anchor 204 through to substrate 101. Bottom plate 103 is fabricated to electrically connect to a bottom plate electrode 215 while top plate 110 is fabricated to electrically connect to a top plate electrode 218. Bottom electrode 215 acts as a common lead for capacitor sensor 200 in completing a sensing circuit. Top electrode 218 is typically attached to a bonding pad for connectivity to a readout chip capable of measuring capacitance.

Figure 3:
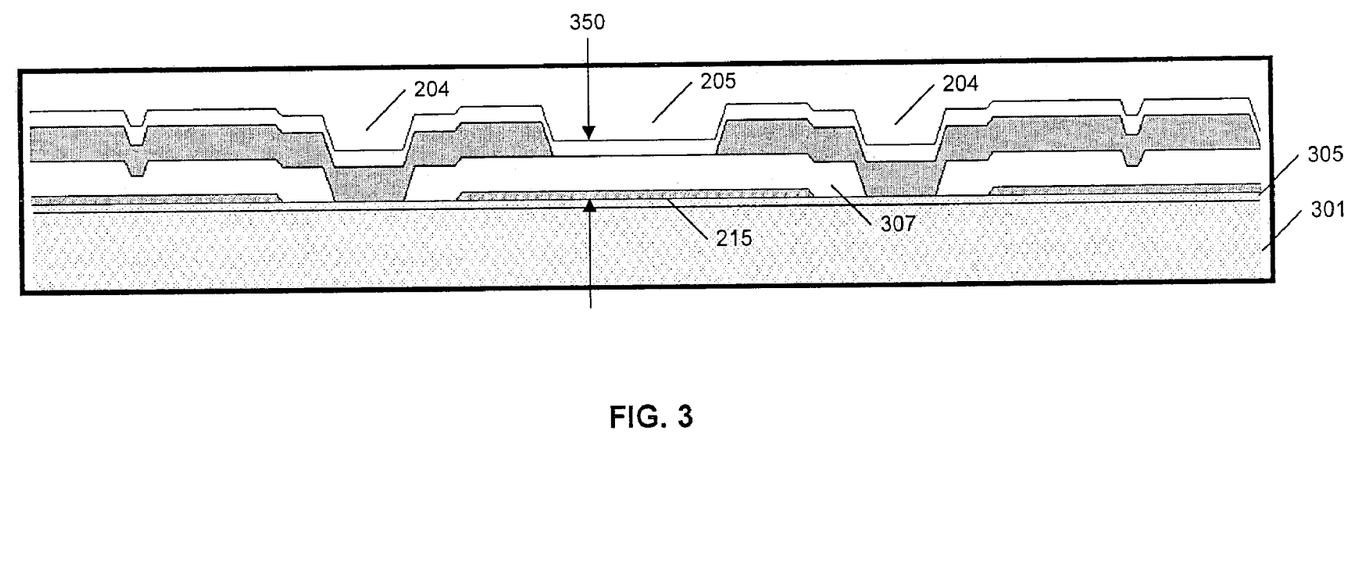
FIG. 3 is a cross-sectional view along A–A' of FIG. 2.

FIG. 3 is a cross-sectional view along A–A' of FIG. 2 showing the layers that comprise capacitor sensor 200. The continuity of bottom plate electrode 215 is interrupted by anchors 204 that pierce through bottom electrode 215 making contact with isolation layer 305. Fill hole 205 provides access to bottom plate electrode 215 for injection of dielectric into the sensing gap region 307 left vacant by the etching of a sacrificial layer.

Figure 4:
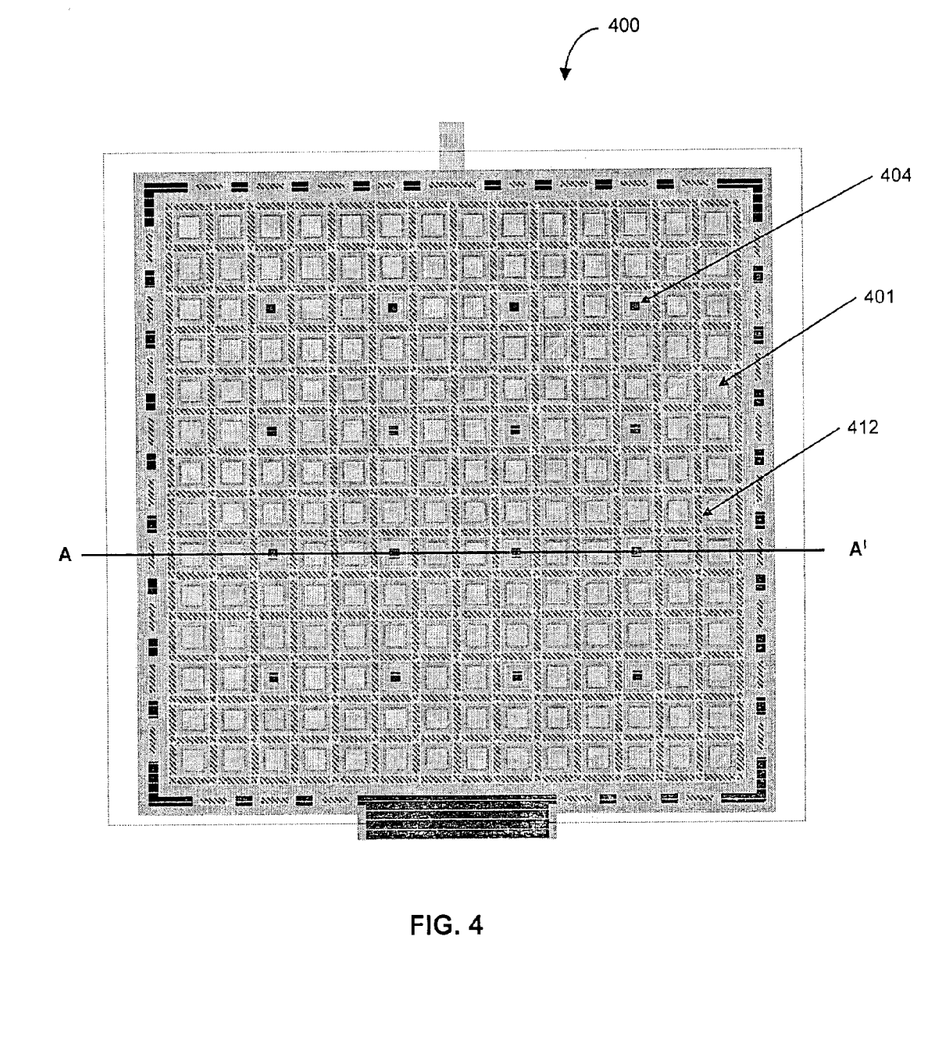
FIG. 4 is a top-level view of a rectangular-shaped fixed parallel plate capacitor sensor having a support layer and implemented according to an embodiment of the invention.

FIG. 4 is a top-level view of a rectangular-shaped fixed parallel plate capacitor sensor having a support layer and implemented according to an alternative embodiment of the present invention. In this implementation, capacitor sensor 400 comprises pores 401 interspersed across the surface of top-plate 110 in a checkered fashion. Anchors 404 are evenly spaced across the device surface, providing extended rigidity between top plate 110 and bottom plate 103.

Figure 5:
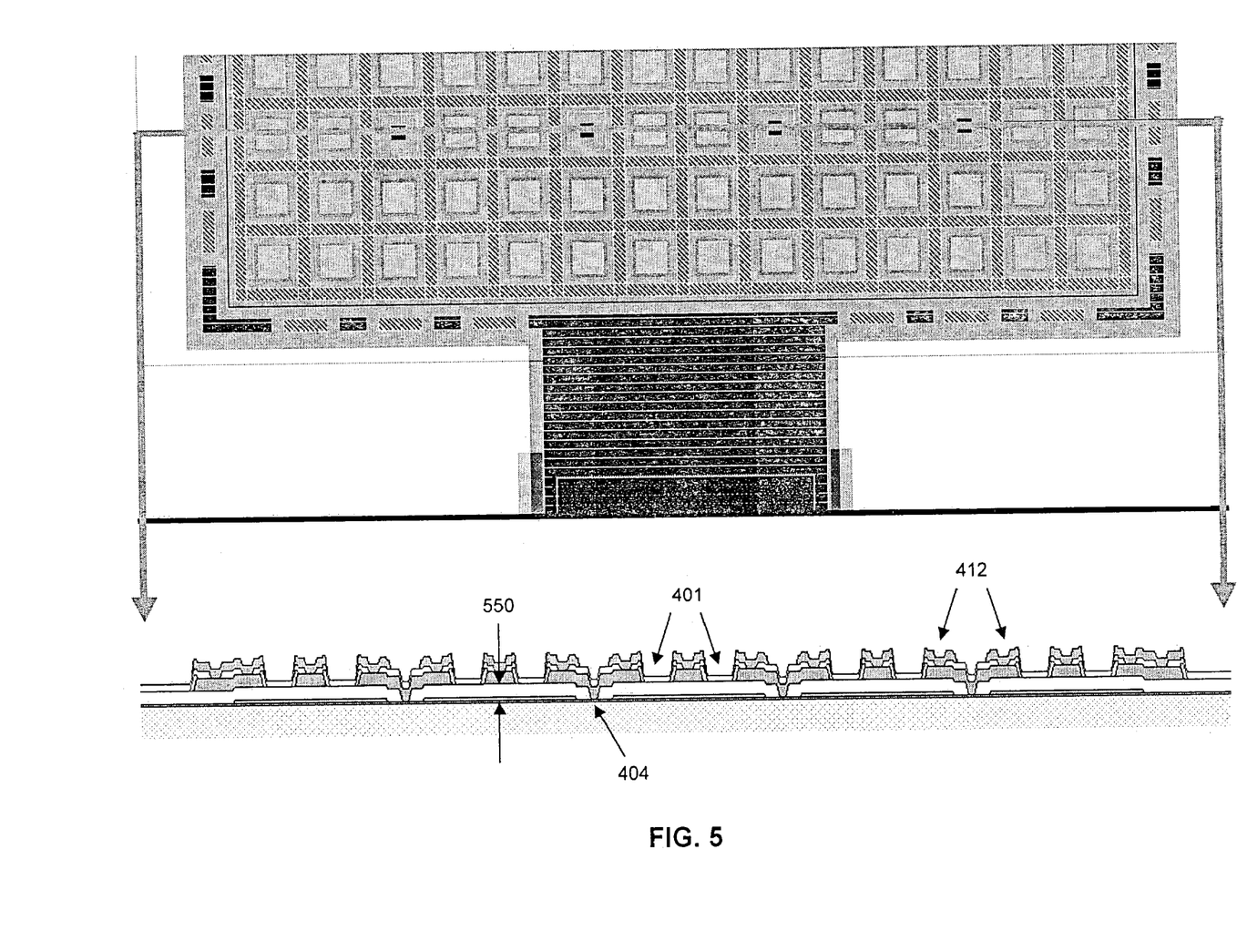
FIG. 5 is a cross-sectional view along A–A' of FIG. 4.

FIG. 5 is a cross-sectional view along A–A' of FIG. 4 showing the layers that comprise capacitor sensor 400. The larger number of anchors 404 in this embodiment permit a smaller sensing gap 550 than the sensing gap 350 created by the previous embodiment of FIGS. 2 and 3. Laboratory results have produced a device of this nature with a sensing gap 550 of 2.0 microns.

The larger number of pores 401 in top plate 110 can make dielectric injection easier in some cases, as well as offer more efficient chemical absorption during device operation. In other cases, however, a strong polymer/solvent interaction chemistry will make a circular fill hole 205 a more efficient structure for forcing a mildly viscous liquid dielectric through pores. The grid-shaped support layer 412 further adds strength to the sensor in this embodiment. The perimeter of the device can be perforated to allow for more efficient filling by allowing more air escape holes.

Figure 6:
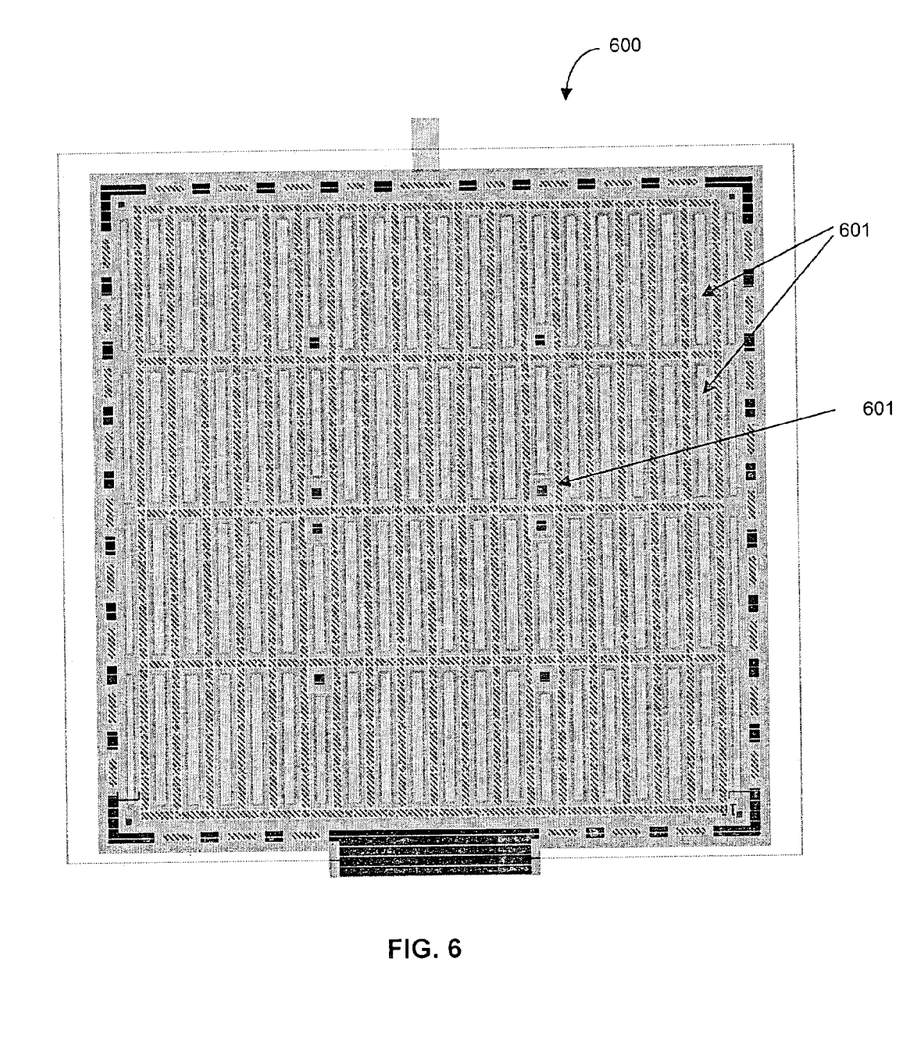
FIG. 6 shows a top-level view of a rectangular-shaped fixed parallel plate capacitor sensor having a pattern of slotted top plate pores and implemented according to an embodiment of the invention.

A variety of different top-plate pore configurations and device anchor arrangements is contemplated by the present invention. FIG. 6, for instance, illustrates yet another top-level view of a rectangular-shaped fixed parallel plate capacitor sensor 600 having a pattern of pores in top plate 110 fashioned using a series of slots 601. Fewer anchors 604 are needed in this embodiment because of the support characteristics of the slotted pores.

Many factors contribute to the overall design goal of providing a pair of plates, parallel in orientation, which maintain their rigidity as the polymer dielectric begins to swell under atmospheric condition. In general, a trade-off exists between the strength provided by a tighter pattern of small pores and the ease with which polymer dielectric can be injected underneath top plate 110. More pores in top plate 110 can mean more anchors will be needed between plates to negate the flexibility of the top plate and the effects of swelling. The pore geometry of the device thus is an important factor in meeting design constraints.

Figure 7:
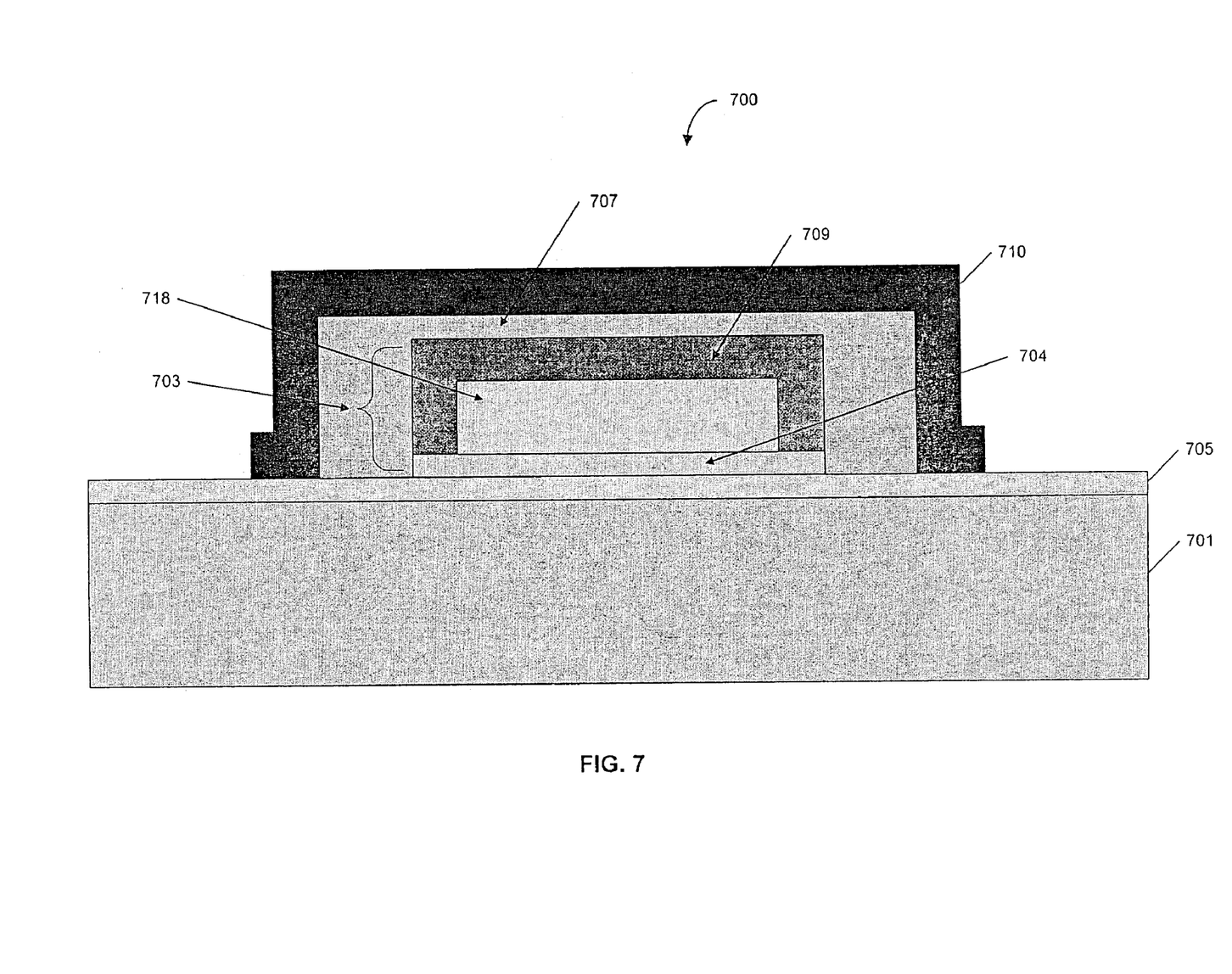
FIG. 7 is a cross-sectional view of a fixed parallel plate capacitor sensor having a dual-layer sealed bottom plate in accordance with the devices and methods of the present invention.

FIG. 7 is a cross-sectional view of a fixed parallel plate capacitor sensor having a dual-layer sealed bottom plate according to the devices and methods of the present invention. Capacitor sensor 700 is a layered device comprising dual-layer bottom plate 703, porous top plate 710, dielectric 707, and built on substrate 701 to be electrically isolated therefrom by isolation layer 705. Support for device 700 is substantially provided by dual-layer sealed bottom plate 703 in this embodiment. Bottom plate 703 comprises first bottom layer 704 deposited onto isolation layer 705, followed by a second bottom layer 709, which together form a sealed area 718 between the two bottom layers. The net result is a raised bottom plate, which reduces the gap distance. This type of device allows different gaps for various arrayed devices in a single process. Narrow gaps may be necessary or at least advantageous for low-dielectric or low-sensitivity polymers.

Figure 8:
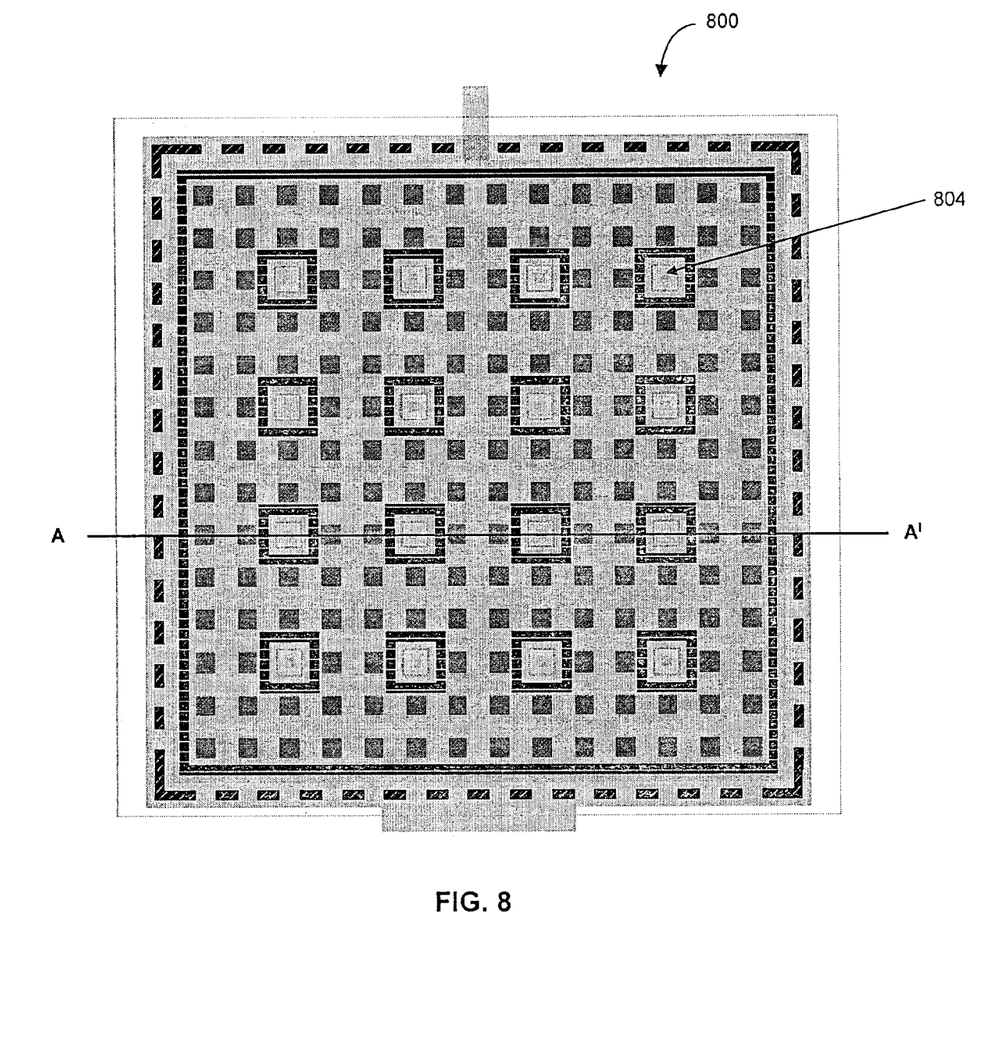
FIG. 8 is a top-level view of a rectangular-shaped fixed parallel plate capacitor sensor having a dual-layer sealed bottom plate and implemented according to an embodiment of the invention.

FIG. 8 is a top-level view of the fixed parallel plate capacitor sensor 700 of FIG. 7 having a dual-layer sealed bottom plate 703 and implemented according to an embodiment of the present invention. From this view are visible the larger anchor regions 804 contemplated by this embodiment. Larger anchors 804 account for the added strength of this embodiment, which in turn permit a smaller sensing gap between top plate 710 and bottom plate 703 without requiring an added support layer such as 112.

Figure 9:
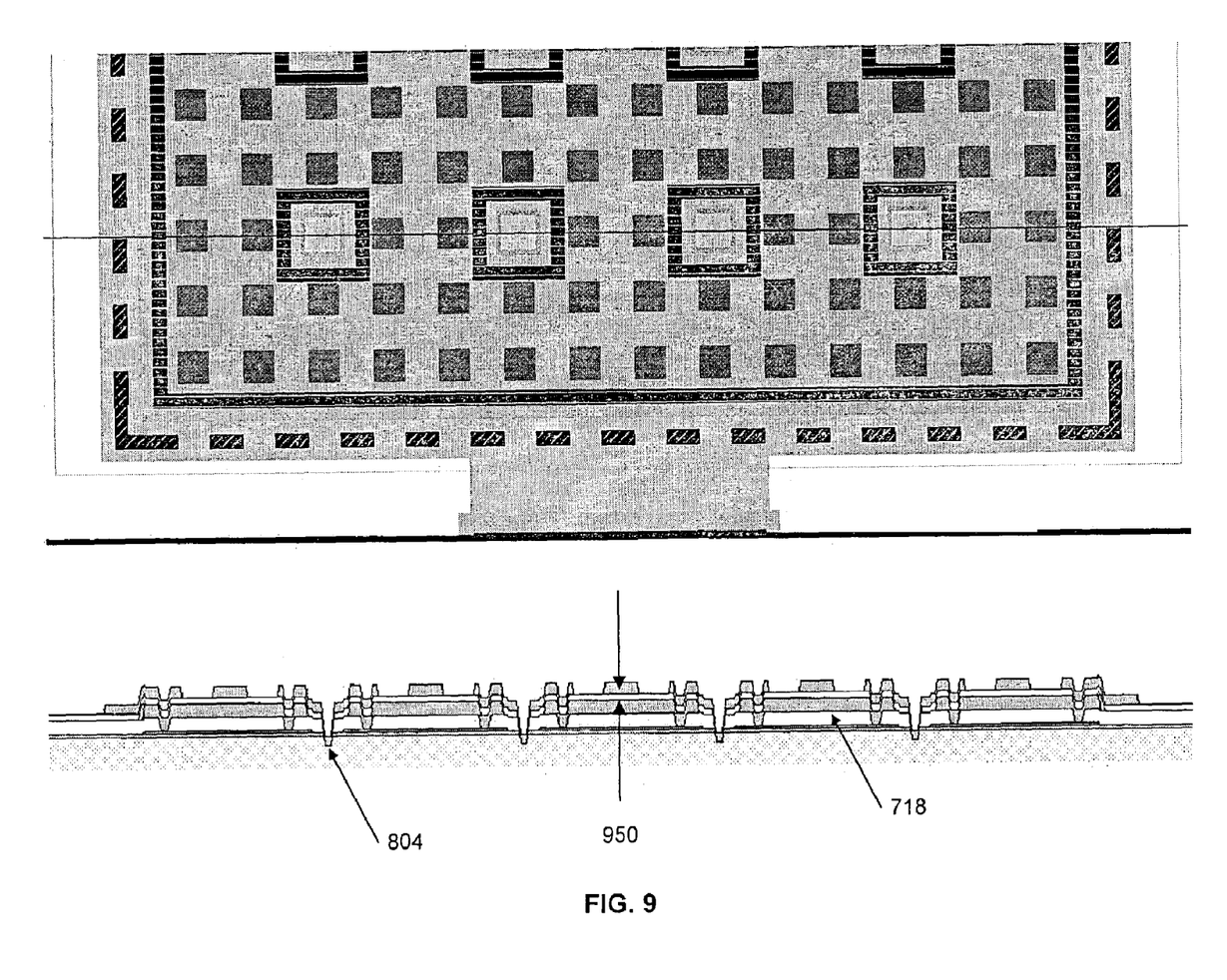
FIG. 9 is a cross-sectional view along A–A' of FIG. 8.

FIG. 9 is a cross-sectional view along A–A' of FIG. 8 showing the layers that comprise capacitor sensor 800 showing both the smaller sensing gap 950 and the sealed areas 718 between bottom layers 704 and 709. Laboratory results have produced a device of this nature with a sensing gap 950 of 0.75 microns.

Figure 10:
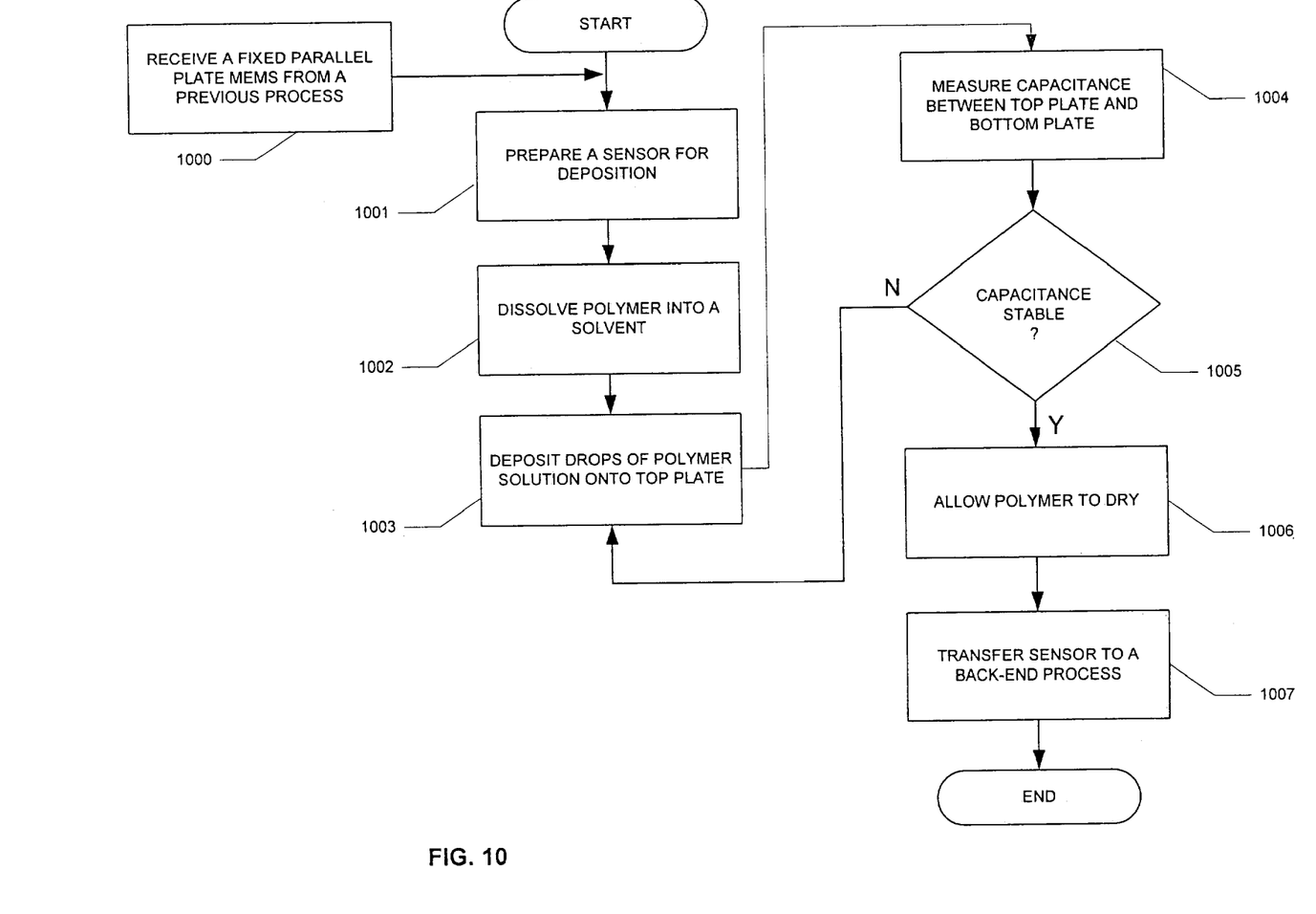
FIG. 10 is a flow diagram illustrating a method for depositing a polymer dielectric between two fixed parallel plates of a capacitor sensor according to an embodiment of the invention.

FIG. 10 is a flow diagram illustrating a method for depositing a polymer dielectric between two fixed parallel plates of a capacitor sensor in accordance with one embodiment of the invention. The process begins with step 1000 where a pre-fabricated, micro-machined fixed parallel plate capacitor sensor is delivered from a previous process and whose sensing gap has not yet been filled with sensing material. In step 1001, a sensor, such as the sensor of FIG. 2, is prepared for polymer deposition. Preparation details depend largely on the particular laboratory processes to be used in the following steps. For instance, preparation step 1001 can include making any electrical connections necessary to effectuate monitoring of the capacitance in steps 1004 and 1005 to follow, as well as dicing the wafer containing the sensor devices. In step 1002, a polymer dielectric to be deposited between the plates of the sensor is dissolved into a solvent. The solvent can be, for instance, chloroform, water, acetone, toluene, methanol, or any other suitable solvent that will permit the polymer/solvent mixture to flow through a fill hole 205 and/or pores 201 in porous top plate 110. A typical polymer concentration in solution is between 0.075 percent and 1 percent by weight.

In step 1003, the polymer/solvent drops are deposited onto or near any one of the pores created in top plate 110. In the embodiment of FIG. 2, polymer injection is easily accomplished by depositing one or more drops of polymer over the larger, central injection hole. For a highly viscous polymer/solvent mixture, injection of dielectric material through injection hole 205 or top plate pores 201 can be accomplished by an inkjet-style injector. For larger drops, such as are characteristic of a solid polymer, a syringe can be used for polymer injection. Using either technique, the goal is a complete polymer coating of bottom plate 103. To achieve a complete polymer coat, inkjet injection usually requires more drops than a syringe because inkjet nozzles are capable of delivering a smaller sized drop. Lab results have shown that an inkjet process can take up to 1000 drops to achieve complete coverage, whereas a syringe can take as few as 5 comparatively larger drops.

The drops are allowed to filter down through pores 201, coming to rest onto bottom plate 103 in the form of a uniform coat over the surface of bottom plate 103 and filling sensing gap 350 created thereunder by the etch of a sacrificial layer during the previous sensor fabrication process of step 1000. In one embodiment, polymer is drawn into sensing gap region 307 by capillary action, displacing the air and changing the dielectric properties of the capacitor sensor in the process. In another embodiment, a spin coat, spray coat, or dip coat is contemplated for achieving greater uniformity of the polymer layer. As a byproduct of deposition, the solvent will evaporate, leaving behind a wet layer of polymer.

In step 1004, the capacitance between top plate 110 and bottom plate 103 is measured and used to monitor and control the deposition of polymer in step 1003. If the measured capacitance in step 1004 is increasing, then deposition continues with more drops of polymer solution added (step 1003) until the measured capacitance stabilizes or reaches a desired value (step 1005). Once a stable capacitance is measured between top plate 110 and bottom plate 103 in step 1005, then polymer deposition stops and processing continues with step 1006.

In step 1006, the device is passed through a post-deposition bake wherein the polymer is dried and readied for back-end processing and packaging in step 1007. Bake step 1006 will dry away remaining solvent that did not evaporate during deposition step 1003. Post-deposition bake usually occurs in an oven at a temperature of about 110 degrees Centigrade and lasts between 10 and 60 minutes. Bake step 1006 is particularly useful for softening a solid polymer so that the polymer uniformly fills the sensor gap and displaces as much air as possible.

Excess polymer can sometimes runoff during deposition step 1003 and therefore needs to be contained in order to prevent polymer escaping the device boundary. Polymer run-off is particularly acute when making device arrays where run-off can interfere with a nearby device. Containment is accomplished by strategic placement of containment barriers to prevent dielectric deposited onto one sensor from interfering with the dielectric of another sensor. In one embodiment, polymer containment is accomplished using a network of troughs to trap excess run-off during polymer deposition. In another embodiment, polymer containment is accomplished using a network of rims to isolate neighboring sensors, as explained to follow.

Figure 11:
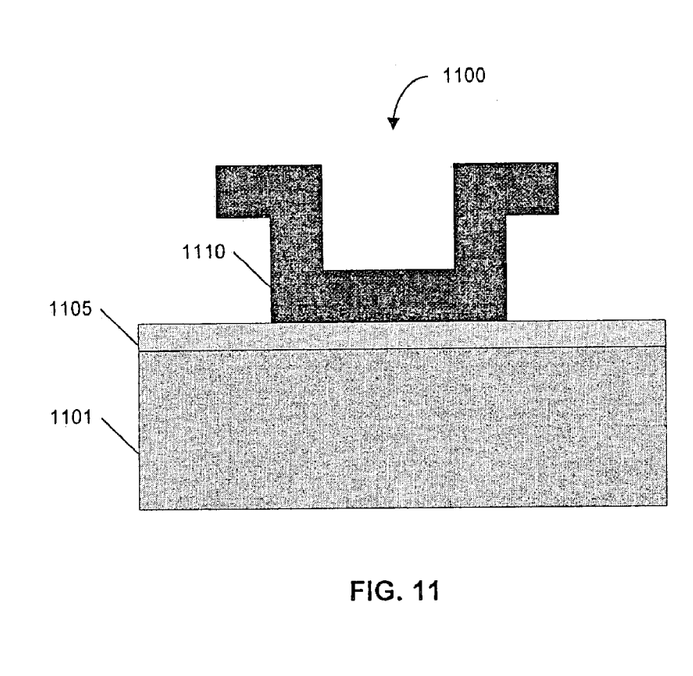
FIG. 11 illustrates a sample containment barrier implemented as a rim in accordance with the devices and methods of the invention.
Figure 12:
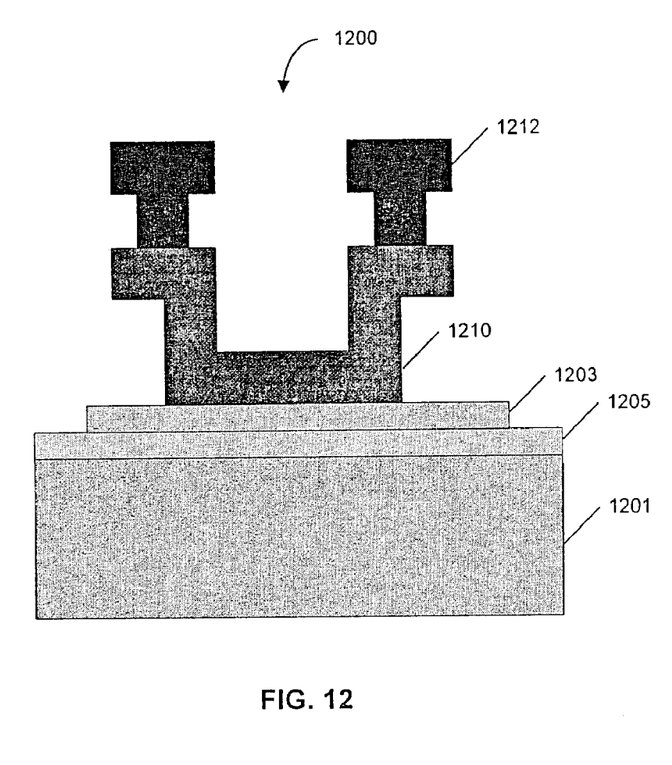
FIG. 12 is an exemplary view of a rim implementation of a containment barrier having three polycrystalline semiconductor layers.

FIG. 11 illustrates a sample containment barrier implemented as a rim in accordance with the devices and methods of the present invention. Rim 1100 is built on a portion of substrate 1101 between neighboring capacitor sensor devices and electrically isolated therefrom by isolation layer 1105. In one embodiment, the rim is made from a polycrystalline semiconductor, such as polycrystalline silicon, preferably co-deposited with an existing layer so as to avoid redundancy in fabrication. FIG. 12 is an exemplary view of a rim implementation of a containment barrier having three polycrystalline semiconductor layers. Rim 1200 is built on a portion of substrate 1201 between neighboring capacitor sensor devices and electrically isolated therefrom by isolation layer 1205. In this embodiment, containment rim 1200 comprises three polycrystalline semiconductor layers, each layer of rim 1200 is preferably co-deposited contemporaneously with a layer during fabrication of the sensor of FIG. 2. Layer 1203 of containment barrier 1200 is co-deposited during deposition of bottom plate 103. Likewise, layer 1210 is co-deposited during deposition of porous top plate 110 and layer 1212 is co-deposited during deposition of support layer 112. As with the sensor devices themselves, co-deposition of layers 1203, 1210, and 1212 comprising containment barrier 1200 can use standard photolithography.

Figure 13:
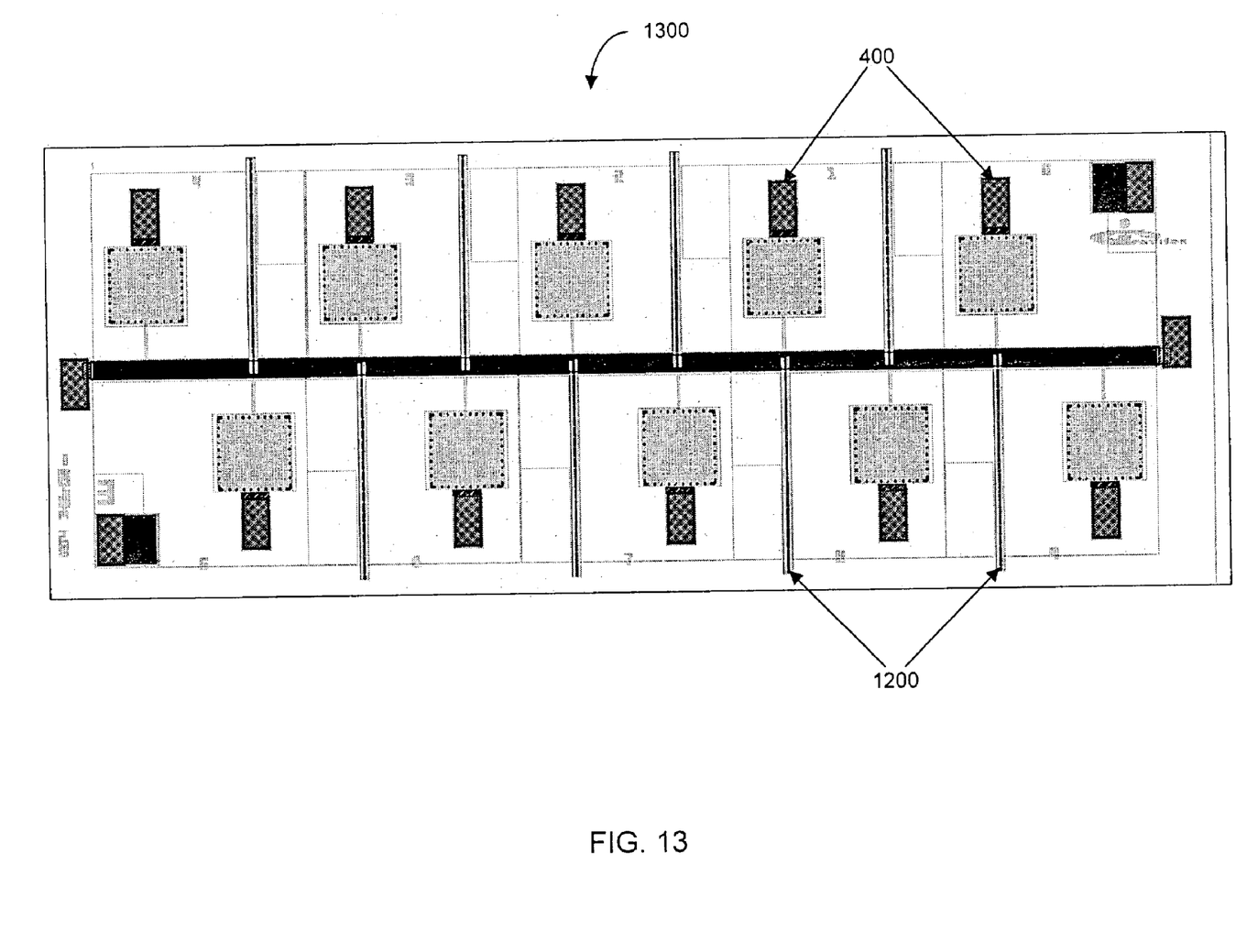
FIG. 13 exemplifies a fixed parallel plate sensor array comprising a plurality of capacitor sensors separated from each other by a network of containment barriers.

In one embodiment of the present invention, a fixed parallel plate capacitor sensor of the kind disclosed herein can be manufactured as an array of devices. FIG. 13 exemplifies a fixed parallel plate sensor array 1300 comprising a plurality of capacitor sensors 400 separated from each other by a network of containment barriers 1200. A sensor array is advantageous for several reasons. First, by manufacturing each device dielectric to have an incrementally different dielectric constant, an array can be tuned to sense those chemicals whose behavior changes in accordance with varying dielectric properties. Second, each device in an array could be manufactured with a different dielectric material, thereby permitting the array to sense multiple different chemicals. Thus, varying the selected material and/or dielectric constant of each device in an array can increase chemical sensitivity and/or improve selectivity of the array. Such a sensor array can be comprised of a variety of sensor devices.

While the particular devices and methods herein shown and described in detail are fully capable of attaining the above described objects of the this invention, it is to be understood that the description and drawings presented herein represent a small number of embodiments of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

What is claimed is:

1. A fixed, parallel plate capacitive microsensor comprising:
   a bottom plate electrode disposed on a substrate;
   a porous top plate electrode disposed in fixed, spaced relation to the bottom plate electrode; and
   a dielectric disposed between said bottom plate electrode and said top plate electrode and through said porous top plate electrode.

2. The microsensor of claim 1, wherein said porous top plate electrode is fabricated with pores using standard photolithography.

3. The microsensor of claim 1, further comprising one or more support layers deposited onto said porous top plate electrode.

4. The microsensor of claim 1, wherein said bottom plate electrode is a drive electrode.

5. The microsensor of claim 1, wherein said bottom plate electrode is a dual-layer electrode.

6. The microsensor of claim 1, wherein said dielectric is selected from the group consisting of a polymer, a ceramic, and a solgel.

7. The microsensor of claim 1, wherein said porous top plate electrode is made from a polycrystalline semiconductor material or a metal.

8. The microsensor of claim 1, wherein said bottom plate electrode is made from a polycrystalline semiconductor material or a metal.

* * * * *